United States Patent [19]
Sachetto

[11] Patent Number: 6,004,546
[45] Date of Patent: Dec. 21, 1999

[54] PHARMACEUTICAL COMPOSITION CONTAINING BISMUTH-POLYACRYLIC ACID COMPOUNDS

[75] Inventor: Jean-Pierre Sachetto, Ziefen, Switzerland

[73] Assignee: Medeva Europe Limited, London, United Kingdom

[21] Appl. No.: 09/308,161

[22] PCT Filed: Nov. 14, 1997

[86] PCT No.: PCT/GB97/03146

§ 371 Date: May 14, 1999

§ 102(e) Date: May 14, 1999

[87] PCT Pub. No.: WO98/22116

PCT Pub. Date: May 28, 1998

[30] Foreign Application Priority Data

Nov. 15, 1996 [GB] United Kingdom .................. 9623962

[51] Int. Cl.⁶ .................. A61K 31/74; A61K 31/29; C07F 9/94
[52] U.S. Cl. .................. 424/78.01; 556/77; 556/79; 514/503
[58] Field of Search .................. 556/77, 79; 514/503; 424/78.01

[56] References Cited

U.S. PATENT DOCUMENTS 5,601,848  2/1997  Marshall .................. 424/653

FOREIGN PATENT DOCUMENTS

| 0 351 987 | 1/1990 | European Pat. Off. . |
| 2 703 250 | 10/1994 | France . |
| WO 92 01457 | 2/1992 | WIPO . |
| WO 95 20970 | 8/1995 | WIPO . |

*Primary Examiner*—Porfirio Nazario-Gonzales

[57] ABSTRACT

An essentially water-insoluble compound of bismuth and polyacrylic acid disperses well in the bowel and forms a good mucoadhesive covering of the bowel wall. Thus in patients with inflammatory bowel disease the bismuth is held in intimate contact to the inflamed tissue of the bowel. Two processes are provided for preparing said water-insoluble compounds.

25 Claims, 3 Drawing Sheets ly still no more than about 1% w/w and most
PHARMACEUTICAL COMPOSITION CONTAINING BISMUTH-POLYACRYLIC ACID COMPOUNDS This invention relates to an essentially water-insoluble compound of bismuth and a polyacrylic acid, use of same for treatment of conditions of the alimentary tract, particularly inflammatory bowel disease and processes for the preparation of said bismuth-polyacrylic acid compounds.

Polyacrylic acid and sodium salts thereof are disclosed in GB-A-2220855 for the treatment of inflammatory bowel disease.

Bismuth compounds are known to treat various medical disorders, such as the treatment of gastric and duodenal ulcers. More recently WO 92/01457 disclosed a bismuth-carbomer compound for the treatment of conditions of the alimentary canal particularly certain inflammatory bowel diseases such as ulcerative colitis and Crohn's disease. Since the carbomer was mucoadhesive, it could hold the bismuth in contact with the diseased bowel wall. The bismuth content of the water-soluble compound of WO 92/01457 was reported as 8.74% w/w and 15.2% w/w (example 4).

The compounds of WO 92/01457 are formed by mixing bismuth salts and polyacrylic acid in aqueous media then neutralising the media to allow reaction. At this point the compound is present as a viscous gel which can then be used as an enema. The compound was precipitated using a water-miscible solvent such as methanol. The resulting powder, however, is difficult to formulate and gives inadequate dispersion and covering of the bowel wall. Furthermore, the process is not very economical on an industrial scale because of the difficulty in handling and separating the high viscosity gel-like compound, the low yield and the high volume of solvent used.

WO 95/20970 describes a more economical process for preparing a water-soluble compounds of bismuth and polyacrylic acid. In the improved process, polyacrylic acid is dispersed in a solution of alkali or ammonia in a water-miscible organic solvent such as methanol or ethanol, bismuth salt is added to this dispersion, and then water or a water-miscible organic solvent is added to the dispersion and the resultant medium left for several days to form a water-soluble compound of bismuth and polyacrylic acid. Finally the resulting slurry of compound is filtered, washed in aqueous ethanol, then dried to form a free-flowing powder. This powder can then be used in gelatin capsules, but like the compound of WO 92/01457 will not give an adequate covering of the bowel wall when given orally. The compounds of bismuth and polyacrylic acid of WO92/01457 and WO95/20970 are hereinafter referred to as the compounds of the prior art.

FR-A-2703250 discloses a gel-forming or dispersible dosage form consisting of a water-insoluble basic bismuth salt and gel-forming agent which is diluted with a diluent or inert vehicle. The specified gel-forming agents include polyacrylic acids and specifically certain Carbopols. Polyacrylic acid must be reacted with a base to form a gel, and accordingly an aqueous dispersion of the polyacrylic acid is added to a suspension of the bismuth salt in an aqueous solution of an amine. Other gel-forming agents disclosed are guar gum, xanthan gum and polyacrylamide, which do not have functional acid groups.

It is an object of the present invention to provide an improved compound of bismuth and polyacrylic acid over those discussed herebefore, more particularly to provide an improved dispersion in the bowel and covering of the bowel wall.

It is a further object of the invention to provide a good mucoadhesive compound of bismuth and polyacrylic acid.

We have now discovered compounds of bismuth and polyacrylic acid which are physically distinguishable from the prior art compounds discussed herebefore, and which have greatly improved physical and pharmacological properties.

Accordingly in a first aspect of the present invention there is provided an essentially water-insoluble compound of bismuth and a polyacrylic acid (hereinafter referred to as compounds of the invention).

By essentially insoluble we mean having a solubility of no more than about 0.5 g$l^{-1}$, preferably no more than about 0.1 g$l^{-1}$, most preferably no more than about 0.01 g$l^{-1}$ in pure water at 25° C. The solubility of the prior art bismuth-polyacrylic acid compounds of WO 92/01457 and WO 95/20970 are thought to be at least about 10 g$l^{-1}$.

Significantly, the present compound forms a good dispersion in the bowel and coats the bowel wall better than the compounds of the prior art. It also has a very good mucoadhesivity to the bowel wall, which has the advantage of holding the bismuth in contact with the inflamed bowel wall. The invention is therefore a major advance over the compounds of the prior art, and in particular when the compounds of the invention are given orally, for delayed release in the bowel.

Although it is contemplated that further polyvalent anions other than bismuth, (particularly metal anions such as calcium, magnesium or barium) may be present on carboxylate moieties of the polyacrylic acid, it is preferred that the compounds of the invention consist essentially of bismuth and polyacrylic acid.

In a preferred embodiment, the compounds of the invention has absorption bands in the infra-red spectra at about 1550 cm$^{-1}$ and about 1720 cm$^{-1}$. The absorption band at 1550cm-1 corresponds to a carboxylate group and is also present in both the prior art compounds of WO 92/01457 and WO 95/20970. However, the band at 1720 cm$^{-1}$ which corresponds to a free carboxylic acid moiety is not present in the infra-red spectra of the aforementioned prior art compounds.

It will be appreciated that the aforementioned bands in the i.r. spectrum can shift depending on how the spectrum is performed. Preferred compounds of the invention will, however, generally have corresponding carboxylate and free carboxylic acid bands such as shown in the accompanying FIGS. 1 and 2.

The compounds of the invention include bismuth salts of polyacrylic acid.

The compounds of the invention also have a much lower monovalent anion content, particularly alkali metal content, than the prior art soluble compounds and preferably have no more than about 4% w/w, more preferably no more than about 3% w/w, more preferably still no more than 20% w/w, more preferably still no more than about 1% w/w and most preferably no more than about 0.5% w/w monovalent anion content. Examples of alkali metal in the prior compound are potassium and sodium (predominantly) and both of these are in very low content in the present compounds. The compounds of the invention are therefore less likely to cause hypertension in long term use than the prior art compounds.

The cation (such as citrate) deriving from the bismuth salt used, can also be in much lower quantities in the present compounds than in the compounds of the prior art. The preferred % w/w of such cations in compounds of the invention are as shown above for monovalent anions.

The w/w bismuth content in the compounds of the invention is normally higher than the exemplified prior art compounds of WO92/01457 and WO95/20970. Preferably the bismuth content in dry solid form of compounds, of the invention is at least 20% w/w, more preferably at least 25% w/w, more preferably still 30% w/w, more preferably still at least 35% and most preferably at least 38% w/w. The maximum bismuth content that has been achieved to date is about 42% w/w. When a compound of the invention is dispersed in aqueous media and prepared as an enema, the amount of bismuth per unit volume is normally also greater than the exemplified prior art compounds, which provides a more potent enema.

Without being bound by theory, it is believed that the bismuth of the invention exists as $Bi^{3+}$. Preferably the ratio of bismuth to carboxylic groups in the polyacrylic acid is 1:6 to 1:3, more preferably at 1:5 to 1:3 (more particularly 1:3.5) and most preferably about 1:3.5.

Preferably, the polyacrylic acid is a carbomer, such as those described in the British Pharmacopoeia and defined in CAS 54182-57-9, which generally consists of a high molecular weight polymer of acrylic acid cross-linked with alkyl ethers of sucrose or with alkyl ethers of pentaerythritol. Carbomers contain about 60% carboxylic acid groups, which is approximately one carboxyl group per 72 molecular weight units. Preferred carbomers are Carbopol 934P and 974P (available from Goodrich UK).

A second aspect of the invention provides a process for preparing a compound of bismuth and polyacrylic acid according to the first aspect of the invention, said process comprising reacting a bismuth containing compound with a polyacrylic acid in an aqueous medium (preferably water) in the presence of a base then acidifying the resulting medium or treating the reaction product with acid to precipitate a compound of bismuth and polyacrylic acid according to the first aspect of the invention.

Preferably the precipitation pH is from about 1 to about 4, more preferably from about 2 to about 3, and most preferably is a pH of about 2.5. The acid can be any organic or inorganic acid, but is preferably hydrochloric acid. The precipitation time or time of addition of acid is preferably in the range of about 10 seconds to about 30 minutes, more preferably in the range 5 to 15 minutes, and ideally about 10 minutes.

A compound of bismuth and polyacrylic acid is formed by (i) mixing a bismuth compound and polyacrylic acid in an aqueous medium, (ii) then adding base to the aqueous medium to increase the pH of the medium and leaving for a time to allow formation of a bismuth-polyacrylic acid compound. At this stage the compound has not only a high bismuth metal content, but also a high e.g. alkali metal content (such as $Na^+$) from the base.

However the inventor surprisingly found that the e.g. alkali metal ions (such as $Na^+$) could be selectively displaced by acidifying the reaction solution at a pH of between about 1 and about 4. This is surprising since it would have been thought that both the alkali metal and bismuth would have been displaced equally thereby destroying the desired bismuth product.

The displaced alkali metal ions leave free carboxylic acid groups, which can then be identified by an i.r. spectrum.

Advantageously, a bismuth salt is used to prepare a compound of the invention, such as salts of weak inorganic acids or organic carboxylic acids, e.g. selected from bismuth citrate, bismuth carbonate, bismuth subsalicylate and bismuth subgallate. Other salts, such as bismuth subnitrate, and bismuthates, such as tripotassium dicitrato bismuthate, may be used. The compound of the invention preferably comprise Carbopol 974P and bismuth derived from bismuth citrate.

Where bismuth citrate or other salts are used, the anion will be present in solution with the resulting bismuth polyacrylic acid compound, and is preferably removed by dialysis before acidifying the aqueous medium.

The ratio by weight of the bismuth, such as bismuth citrate, to polyacrylic acid for the formation of a compound of bismuth and polyacrylic acid can vary, but advantageously is in the range of about 0.5% to about 1.6% w/w, more preferably about 0.8% to about 1.4% w/w, and most preferably about 1.125% w/w.

The base is added to substantially neutralise the acidic aqueous medium so that the polyacrylic acid becomes more soluble, swells and reacts with the bismuth compound. Preferably the final reaction pH is about 5 to about 8, more preferably about 6 to about 7, and most preferably about 6. The most suitable bases are alkali metal hydroxides, particularly sodium and potassium hydroxide. For example bismuth citrate can be added to an aqueous medium and then polyacrylic acid added and sodium hydroxide used to adjust the pH of the resulting acid medium. Alternatively, the polyacrylic acid may first be neutralised and then the bismuth citrate added.

The theoretical amount of alkali metal hydroxide, such as sodium hydroxide, to be added corresponds to the stoichiometric amount required to neutralise the carboxylic acid groupings of the polyacrylic acid (or carbomer). However some buffering effect is observed in the reaction mixture which would necessitate the addition of more alkali to achieve neutrality. Only 100% of the theoretical amount of sodium hydroxide is used resulting in partial neutralisation.

A suitable reaction time of the bismuth with polyacrylic acid is about 30 minutes to about 24 hours, but ideally is about 1 hour.

In a preferred embodiment there is provided an essentially water-insoluble compound of bismuth and polyacrylic acid comprising:

(i) mixing a bismuth salt (such as bismuth citrate) and a polyacrylic acid in an aqueous medium;

(ii) adding alkali either before, after or simultaneously with the bismuth salt to raise the pH of said aqueous medium to between about 5 and about 8 inclusive and leaving for a period to allow for reaction; and (iii) adding acid to lower the pH to between about 1 and about 4 inclusive to precipitate said insoluble bismuth polyacrylic acid compound.

The precipitate is then washed with an aqueous solution (such as water) to remove by-products of the reaction, filtered and dried to produce a powder. Alternatively, the concentration of anions from the bismuth salt in solution could first be removed by dialysis at step (ii) above, before said precipitation.

In a third aspect of the invention there is provided a process for preparing an essentially water-insoluble compound of bismuth and polyacrylic acid according to the first aspect of the invention, said process comprising reacting a base of bismuth with a polyacrylic acid in an aqueous medium (preferably water).

The compounds of the invention then precipitate from solution without the addition of acid.

Preferably the base of bismuth is bismuth hydroxide.

The compound of the invention can be used to treat conditions of the alimentary canal, but is particularly useful in the treatment of inflammatory bowel disease (i.e. of the small and large intestine) such as Crohn's disease, ulcerative colitis, pouchitis, and diverticulitis.

Thus the dry powder obtained as above can be administered orally, for example in the form of a post-gastric delayed release oral microgranules tablet or capsule, or rectally in the form of an enema or foam enema.

Typical enema formulations comprise an effective amount of water-insoluble compound dispersed in a suitable aqueous flowable carrier vehicle. The carrier vehicle is preferably thickened with natural or synthetic thickeners such as gums, acrylates or modified celluloses and can also comprise an effective amount of a lubricant such as a natural or synthetic fat or oil.

When used orally, the powdered compound can be contained in a gelatin capsule or a tablet which is then film-coated. The film coating is preferably insoluble in the gastric juice and in intestinal juice below about pH5, but soluble in the ileum juice so that the bismuth-polyacrylic acid compound is deposited at the diseased site in the ileum or the colon. Such a capsule is described in EP-A-0 097 651 (the teaching of which is incorporated by reference). Alternatively the compound can be formed into microgranules and film-coated such as described in U.S. Pat. No. 5,401,512 (incorporated herein by reference). Suitable film coating resins are methacrylate and methacrylic acid polymers such as sold under the trade name Eudragit™, such as Eudragit™ L or S, cellulose acetate phthalate (CAP), polyvinyl acetate phthalate (PVAP) and hydroxypropyl methylcellulose phthalate. In general the thickness of the film-coating of a gelatin capsule is 25 to 200 µm, preferably 3 to 25 µm. In microgranular film-coated formulations, suitably the granules are 0.25 to 4 mm, particularly 0.4 to 1.5 mm diameter. A disintegrant such as sodium starch glycolate is advantageously used in the oral formulation of the invention.

The dosage of the bismuth-polyacrylic acid compound in an enema or a foam enema would be in the range 100 mg to 1600 mg (calculated as elemental bismuth), preferably 200 mg to 800 mg, in an aqueous carrier of 20 to 100 ml.

Further aspects of the invention are as follows:

A. An essentially water-insoluble compound of bismuth and polyacrylic acid according to the first aspect of the invention for use in medicine.
B. Use of an essentially water-insoluble compound of bismuth and polyacrylic acid according to the first aspect of the invention in the preparation of a medicament for the treatment or prophylaxis of inflammatory bowel disease.
C. A method for the treatment of inflammatory bowel disease comprising administering to the patient an effective amount of an essentially water-insoluble compound as defined in the first aspect of the invention until a beneficial response is obtained.
D. An essentially water-insoluble compound of bismuth and a polyacrylic acid according to the first aspect of the invention obtainable by mixing bismuth citrate and a polyacrylic acid in an excess of water such as in the range of about 0.5% to about 1.6% w/w, more preferably about 0.8% to about 1.4% w/w, and most preferably about 1.125% w/w, agitating to form an intimate blend of the two products, adding sodium hydroxide and agitating to a pH of between 6 and 7, leaving the viscous dispersion at rest for 1 to 24 hours, then progressively adding 1N hydrochloric acid solution with gentle agitation to the viscous dispersion to a pH of about 2 to 3, isolating and drying the resulting precipitate of said essentially water-insoluble compounds.
E. An essentially water-insoluble compound of bismuth and a polyacrylic acid according to the invention obtainable by dispersing a polyacrylic acid in an excess of water with a homogeniser, adding bismuth hydroxide and strongly homogenising for about a further 10 minutes the resulting milky suspension, leaving over night at room temperature to rest, then isolating and drying the resulting precipitate of said essentially water-insoluble compound.

During the preparation of preferred compounds of the invention, such as illustrated in the examples hereinafter, bismuth citrate (for example) is suspended in water and carbomer (as an example of polyacrylic added). The pH of this suspension is about 3.5. It is milky in appearance. Upon the addition of the theoretical amount of sodium hydroxide, the suspension becomes translucent and viscous (about 6,000 mPa.s). The pH is increased to about 6.4. The theoretical viscosity for this concentration of neutralised carbomer is >80,000 mpa.s.

When the product is dialysed, the viscosity increases (the viscosity of carbomer is reduced in the presence of ions). The dialysis water contained about 1% of the added bismuth, but about 91% of the added citrate.

An alternative method of production was tried where the carbomer was neutralised first and then the bismuth citrate was added. Almost identical results were obtained except that the viscosity before dialysis by this method was lower.

The translucent suspension left after dialysis consisted of solely bismuth, sodium, carbomer and water.

When the gels formed above are acidified to about pH 2.5 with a strong acid such as hydrochloric acid, a white precipitate is formed which, when filtered, washed and dried, contains 35.5% bismuth, 0.09% sodium and 0.04% chloride.

An infra-red spectrum of this material shows that the strong band at $1720 \text{ cm}^{-1}$ corresponding to the carboxylic acid residue of the carbomer is reduced, and has been replaced by significant absorption at $1550 \text{ cm}^{-1}$ corresponding to the carboxylate $COO^-$ of a partially neutralised carbomer. Therefore the carbomer is partially neutralised and in the absence of the sodium, the only other possible counter ion is bismuth or a bismuth molecular ion.

If we now look at the stoichiometry of the preparation, we can see the following:
The reaction mixture contains
579.1 milliatoms of Bi,
1,737.4 meq of $Bi^{3+}$
1,737.4 meq $citrate^{3+}$
2,763 meq COOH in the carbomer (carbopol)
2,763 meq sodium hydroxide.

This gives an approximate ratio of one bismuth to 4.8 carboxyl groups.
Elemental analysis showed C%29.8,H%3.5,Bi% 35.56
Theoretical values for one $Bi^{3+}$ reacting with three $COO^-$ groups out of five is
C%30.7,H%2.9,Bi%35.66
This is reasonably good agreement.

Two further studies have been carried out. In one the ratio of bismuth was increased to 1 Bi:3.5 carboxyl groups. This led to the same type of reaction, and a product having a 41.7% Bi content. The bismuth content was not further increased using a ratio of 1:2.

When the salt is titrated with sodium hydroxide to determine the number of COOH groups, using carbomer as a control, the quantity of COOH groups fits the calculated quantity on the basis of the $BI^{3+}$ ion (rather than BiO or other molecular ion). The results were 39–41% COOH against a theoretical value of 38%.

Further experiments consisted of treating the salt with sodium edetate, where as expected all the bismuth could be extracted by dialysis, demonstrating that any salt is ionic in nature.

The invention will now be illustrated by way of the following examples, and Figures in which.

EXAMPLE 1

Figure 1:
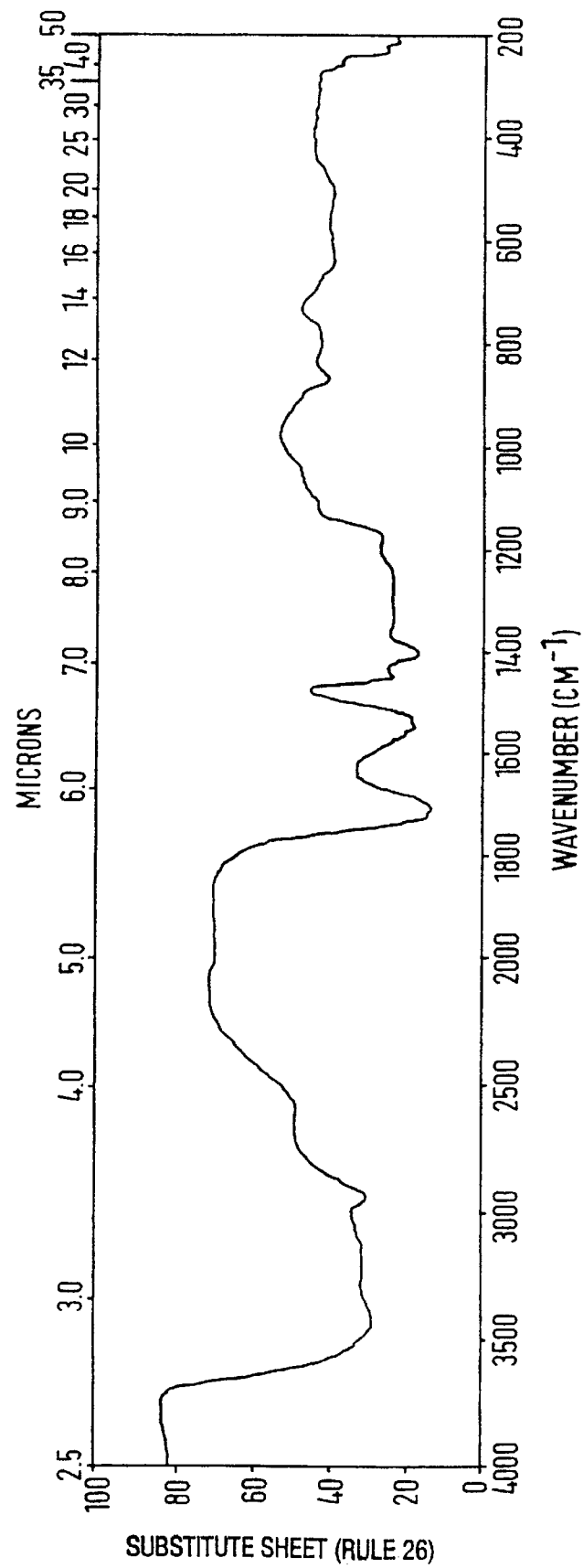
FIGS. 1 and 2 are infra-red spectrum of compounds of the invention.

3500 g of demineralised water was weighed in a 5 liter beaker and 45 g (dry basis) of bismuth citrate were added and suspended in the water by stirring with the propeller of a Silverson homogeniser. To that suspension, 40 g (dry basis) of Carbopol 974 P were added and dispersed by continuing the stirring. To the stirred intimate blend of the two products, a solution of 22.27 g sodium hydroxide in 240 ml water was added, leading to a thick dispersion (viscosity: in the range of 40,000 to 60,000 mPa.s at 20° C. as measured with a Brookfield viscometer type DV-II, equipped with a spindle No. 63 rotating at 1.5 rpm). The viscous dispersion had a pH of 6.2 and it was left to rest at room temperature for one hour.

After one hour at rest, 593 ml of a 1N hydrochloric acid solution was added progressively to the gently stirred viscous dispersion (a gentle stirring with a mechanical stirrer was more suitable than the homogeniser propeller). The viscosity started to drop significantly already when pH 5.0 was reached and at the same time a white fine precipitate appeared. However to complete the precipitation the 593 ml acid was added until pH 2.5 was reached.

The heavy precipitate was left to stand overnight and was separated first from the bulk of the aqueous mixture by decantation and was then re-suspended in the beaker by adding 1600 ml of fresh water. The suspended product was then filtered on a Buchner filtration apparatus using a paper filter (round paper filter LS-14). A further washing took place on the filter, with a total of 1600 ml of water. The filtered product was then placed on a glass plate and left to dry in air at room temperature for 24 hr. Drying was completed in the oven, to a residual water content of 1.5%.

Total recovered weight: 64 g (dry basis).

CHARACTERISATION OF THE PRODUCT

The product appeared as a white free-flowing powder. It had a total elemental bismuth content of 35.31%.

The product was packed into a hard gelatine capsule and was released from the capsule in disintegration and dispersion tests without lump formation, indicating that good dispersion would be obtained in the bowel, and it would provide a good coating over the bowel wall.

The infra-red spectrum showed two characteristic absorption bands : one at 1550 $cm^{-1}$ for the carboxylate grouping and one at 1720 $cm^{-1}$ for the free carboxylic acid grouping. The absorption bands of BiOCl, a possible by-product, were not present on the spectrum indicating its absence as contaminant. The residual chloride content was 0.07%.

The residual Na+ content was 0.211%, and the residual citrate content was 0.16%.

EXAMPLE 2

45 g of bismuth citrate was dispersed in 3500 g of water, 40 g Carbopol 974 P was added and then a solution of 24 g sodium hydroxide in 240 ml water, as above. The solution was then left for two days at rest (room temperature) followed by the addition of 1N hydrochloric acid (789 ml) solution to adjust the pH of the medium to pH 1.5. The resulting precipitate was decanted, re-suspended, and washed as above, then dried and sieved. 54 g of product was recovered, having a residual water content of 1.7% and an elemental bismuth content of 35.34%. Residual $Na^+$: 0.10%, residual citrate: 0.96% .I.R.: The same bands were noted as for the product of Example 1, but with the 1550 $cm^{-1}$ band being smaller and the 1720 $cm^{-1}$ band being larger.

EXAMPLE 3

22.5 g bismuth citrate was dispersed in 475 g of water, 40.0 g Carbopol 974 P was added, followed by 21.5 g sodium hydroxide in 210 ml water. After two days at room temperature, 726 ml 1N hydrochloric acid was added and the resulting precipitate decanted as before. The product was highly swollen and needed to be suspended in acetone to be filtered. The product was then washed on the filter with acetone, and the precipitate dried and sieved. 40 g of product was recovered. Residual water content : 2.2%, elemental bismuth : 23.11%. Na+: 0.44%. I.R. bands at 1500 $cm^{-1}$ (smaller) and 1720 $cm^{-1}$ (larger).

EXAMPLE 4

1975 g of purified demineralised water were poured in a 3 liter beaker and 48 g of bismuth citrate (47.3 g dry basis) were added and suspended in the water by stirring with a Silverson homogeniser. To the suspension, 30 g of Carbopol 974 P (i.e. 29.25 g dry basis) were added and dispersed by continuous stirring. To the blend, a solution of 24 g sodium hydroxide in 240 ml water was added, leading to a thick dispersion (viscosity of about 50,000 cps at 20° C.). The viscous dispersion had a pH of 7.0 and was left to rest at room temperature for two days. Then 800 ml of a 1N hydrochloric acid solution were added progressively to the gently stirred viscous dispersion. The viscosity started dropping at pH 5.0 and a white fine precipitate appeared, the precipitation was completed when the full addition of the acidic solution and pH 1.5 was reached. The precipitate was separated from the supernatant by decantation and it was then resuspended in 500 ml of fresh water in the beaker. Then it was filtered on a Buchner filtration equipment using a filter paper. A further washing took place on the filter with a total of 2,000 ml water. After air-drying on a glass plate, the solid was placed in an oven and dried there until a residual water content of 1.4% as determined by the Karl Fisher method.

Total recovered weight: 52.3 g (i.e. 51.57 g dry basis).

Bismuth content: 41.66%.

The product did not form lumps when released in water from a capsule. The infra-red spectrum showed two characteristic absorption bands at 1550 $cm^{-1}$ and at 1720 $cm^{-1}$. The residual citrate content was: 0.58% and the residual $Na^+$ content was 0.18%.

EXAMPLE 5

236.4 (dry basis) bismuth citrate were reacted with 209.96 g (dry basis) carbomer in 18387 g of water in the presence of 1170 g of a 10% sodium hydroxide solution. The mixture was then stirred for 105 minutes at room temperature. After one hour, 2600 g of 1N hydrochloric acid was added over 10 minutes to the reaction mixture under gentle stirring, pH:2.5 was reached. The precipitate was left to settle overnight and then it was filtered on a Buchner filter. The precipitate was washed on the filter with two portions of 8000 g water, then it was air-dried first and finally dried in the oven. Weight recovered : 323.4 g with a residual water content of 1.7% i.e. 317.9 g dry basis corresponding to a theoretical yield of 96.1%. Bismuth content found : 35.4%. Residual Na+ and residual citrate below 1%. The water solubility was below 0.006 $gl^{-1}$.

The infra-red spectrum of the water-insoluble compound of bismuth and carbomer according to Example 5 is shown in the attached FIG. 1.

The solubility data obtained above was obtained by the following test.

Three samples of said product previously sieved over a 63 micron sieve, are suspended in 100 ml of pure water in a closed glass flask. One sample is placed at room temperature for 1 hour, the second at room temperature for 19 hours and the third at 37° C. for 1 hour. Each suspension is stirred with a magnetic stirrer during the whole test period. Then the suspended solid is left to decant, and the supernatant is centrifuged twice until it was perfectly clear/transparent, free of any residual particles. The three centrifuged solutions are then analysed for bismuth content by atomic absorption (limit of detection : less than 0.3 mg/l Bi).

EXAMPLE 6

2.1 g of Carbopol 974P were dispersed in 184 ml of water with an efficient homogeniser. Then 1.47 g of bismuth hydroxide containing 82.31% of bismuth was added and suspended under homogenisation. A milky suspension was obtained and homogenised for 10 minutes under strong homogenisation.

The mixture was left to rest overnight at room temperature. A white solid separated from the liquid, then it was filtered, washed with 50 ml water on the filter, then air dried and finally dried in the oven at 40° C. under reduced pressure.

Figure 2:
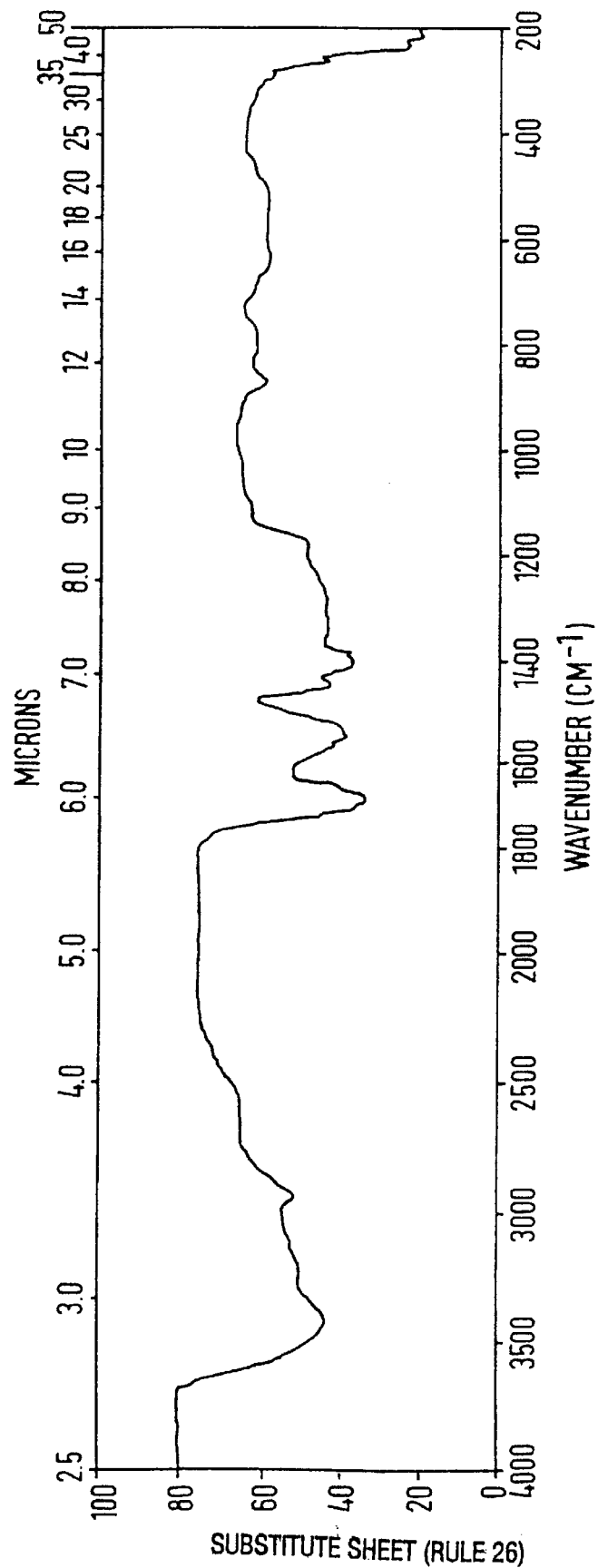

An IR spectrum of the solid was performed and is shown in FIG. 2. The IR shows that the solid product is not bismuth hydroxide, but a product which has absorption bands at 1720 cm−1 and 1550 cm−1 similar to the insoluble bismuth carbomer compound obtained through the treatment of a bismuth carbomer enema with strong acid.

EXAMPLE 7
Dispersion in the Colon

Hard gelatine size 0 capsules were each filled with 300 mg of water-soluble bismuth compound in solid forms as obtained according to:
WO 92/01457 (Rhodes and Evans) : Solid No. 1
WO 95/20970 (Nobel Chemicals) : Solid No. 2 or Example 5: Solid No. 3.

The comparative dispersion behaviour of the three solid compounds was tested by placing each capsule on the surface of a 100 cm³ phosphate buffer solution (pH : 6.5) at 37° C. in a 250 cm³ beaker stirred at 60 rpm by a magnetic stirrer. This simulates the aqueous, pH and motile environment of the colon.

The dispersion behaviour of the three test capsules is summarised hereafter:

| Content of the test capsule | Dispersion behaviour of the content |
|---|---|
| Solid No. 1 | lumps formed - poor dispersion |
| Solid No. 2 | lumps formed - poor dispersion |
| Solid No. 3 | complete dispersion (no lumps) |

Therefore the insoluble bismuth-polyacrylic acid compound of the invention, disperses in the simulated colonic fluid and will coat the walls of the colon whereas the compounds of WO 92/01457 and WO 95/20970 form lumps in the simulated colonic fluid and this will be very poor at coating the colon wall.

EXAMPLE 8

The purpose of this test was to correlate the bioadhesive properties of the prior art (WO 95/20970 sample NR. 1, WO 92/0147 sample NR. 2) with that of the invention, (sample NR. 3).

Colonic samples were obtained from Yorkshire pigs after their sacrifice. Longitudinal sections of the colonic tissue≈4 cm² were gently rinsed with simulated intestinal fluid (without pancreatin) and used immediately. The pH was adjusted at 7.2±0.1 considering the pH value reported by Banker and Rhodes (1996) for the sigmoid colon and rectum.

The bioadhesion measurements were carried out using the method validated by Aguilera et al in 12th Pharmaceutical Technology Conference 1 (1993) 115–131. 500 mg of powder were manually fed into a special die and 2000 psi pressure was applied for 30 seconds for each of the formulations tested (with the exception of NR. 3, for which, 4000 psi pressure was applied) using a laboratory press (carver-Press, Model C). The average diameter (n=10/formulation) was 1.170±0.05 cm.

The tablets were moistened by exposing one face to the simulated intestinal fluid, and measuring at hydration time zero. The adhesion force was measured by placing the tablet (in the absence of pressure), in contact with a circular section of the colonic tissue for 30 sec.

Figure 3:
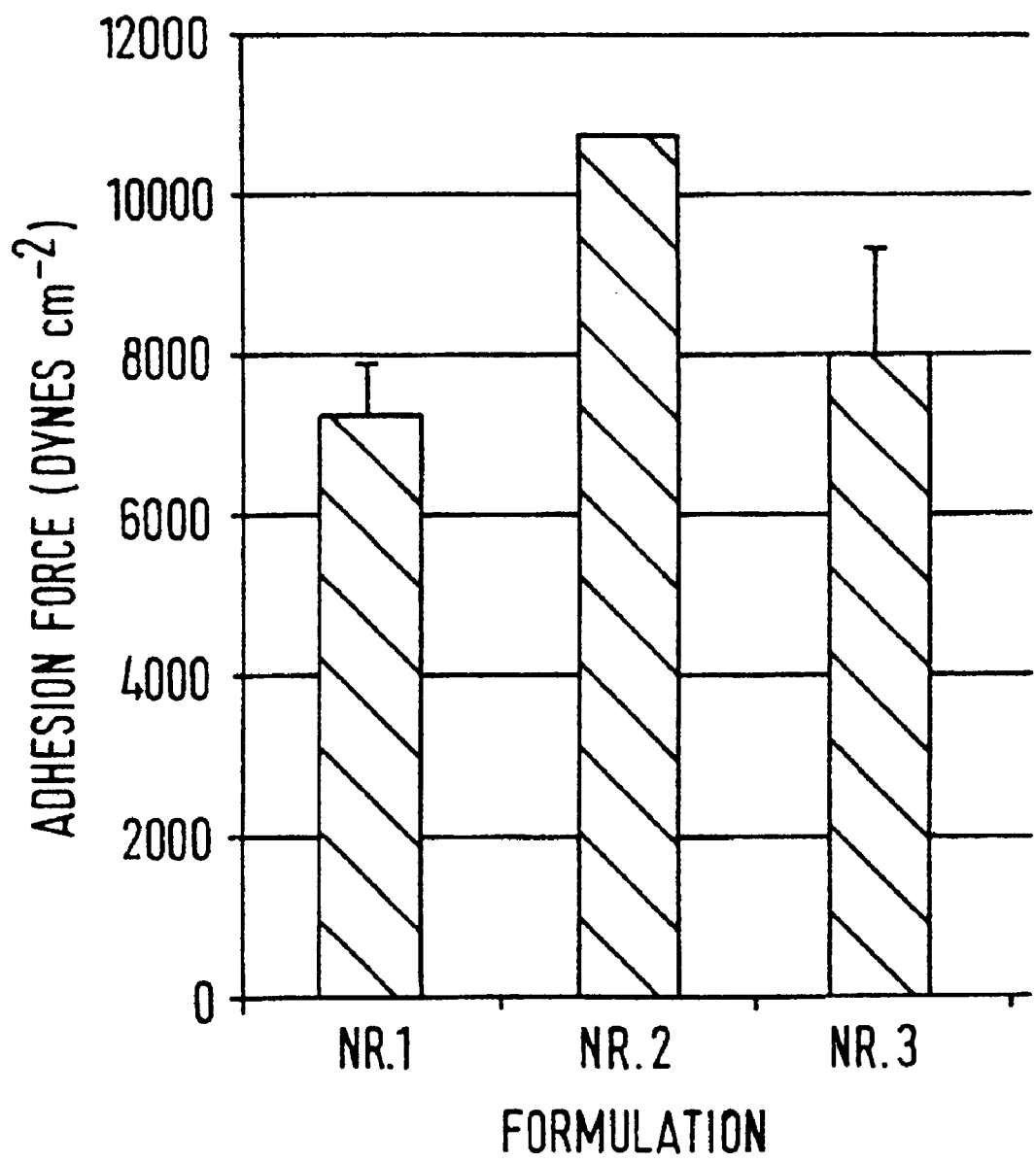
FIG. 3 shows the bioadhesion force of a compound of the invention and prior art compounds.

The tensiometer dial was rotated at a constant rate of 0.5 units/sec and the adhesion force reading was obtained when the sample became detached from the mucosa. All the samples were randomly assayed using their corresponding code number 1 to 3 as defined above. The results are shown in FIG. 3 (n=3; mean±S.D.).

As can be seen, the insoluble bismuth polyacrylic acid compound of the invention has a very good mucoadhesive force and this in combination with its excellent colonic wall covering ability provides a therapeutic advance over the prior compounds.

I claim:

1. An essentially water-insoluble compound of bismuth and a polyacrylic acid having an absorption band in the infra-red spectrum at about 1720 cm$^{-1}$ corresponding to a free carboxylic acid group.

2. The compound according to claim 1 having an additional absorption band in the infra-red spectrum at about 1550 cm$^{-1}$ corresponding to a carboxylate band.

3. The compound according to claim 1 having a bismuth content of at least 20% w/w.

4. The compound according to claim 3 wherein the bismuth content is at least 35% w/w.

5. The compound according to claim 1 wherein the polyacrylic acid is present as carbomer.

6. The compound according to claim 1 having an infra-red spectra essentially as shown in FIGS. 1 and 2.

7. A pharmaceutical formulation comprising an essentially water insoluble compound of bismuth and a polyacrylic acid together with a pharmaceutically acceptable carrier, said compound having an absorption band in the infra-red spectrum at about 1720 cm$^{-1}$ corresponding to a free carboxylic acid group.

8. The formulation according to claim 7 adapted for oral or rectal administration.

9. The formulation according to claim 8 in the form of an enema or foamable enema.

10. The formulation according to claim 9 in the form of a post-gastric delayed release oral tablet, capsule or granules.

11. A process for obtaining an essentially water-insoluble compound of bismuth and a polyacrylic acid having an absorption band in the infra-red spectrum at about 1720 cm$^{-1}$ corresponding to a free carboxylic acid group comprising reacting a bismuth compound with a polyacrylic acid in an aqueous medium in the presence of a base which has been added before, after or simultaneously with the polyacrylic acid and subsequently treating the reaction product with acid to precipitate said bismuth-polyacrylic acid compound.

12. The formulation according to claim 11 wherein the pH of the acid is between about 1 and about 4 inclusive.

13. The formulation according to claim 11 wherein the pH of the acid is between about 2 and about 3 inclusive.

14. The process for obtaining an essentially water-insoluble compound of bismuth and a polyacrylic acid having an absorption band in the infra-red spectrum at about 1720 cm$^{-1}$ corresponding to a free carboxylic acid group comprising reacting a base of bismuth with a polyacrylic acid in an aqueous medium.

15. The formulation according to claim 14 wherein the base of bismuth is bismuth hydroxide.

16. The process for obtaining an essentially water-insoluble compound of bismuth and a polyacrylic acid having an absorption band in the infra-red spectrum at about 1720 cm$^{-1}$ corresponding to a free carboxylic acid group comprising:
(i) mixing a bismuth salt and a polyacrylic acid in an aqueous medium;
(ii) adding alkali either before, after or simultaneously with the bismuth salt to raise the pH of said aqueous medium to between about 5 and about 8 inclusive and leaving for a period to allow for reaction; and
(iii) adding acid to lower the pH to between about 1 and 4 inclusive to precipitate said insoluble bismuth polyacrylic acid compound.

17. The process according to claim 11 wherein the polyacrylic acid is a carbomer.

18. The process according to claim 14 wherein the polyacrylic acid is a carbomer.

19. The process according to claim 16 wherein the polyacrylic acid is a carbomer.

20. A method for the treatment of inflammatory bowel disease comprising administering to the patient an effective amount of an essentially water-insoluble compound of bismuth and a polyacrylic acid, said compound having an absorption band in the infra-red spectrum at about 1720 cm$^{-1}$ corresponding to a free carboxylic acid group.

21. The method according to claim 20 wherein said compound has an additional absorption band in the infra-red spectrum at about 1550 cm$^{-1}$ corresponding to a carboxylate band.

22. The method according to claim 20 wherein said compound has a bismuth content of at least 20% w/w.

23. The method according to claim 22 wherein said compound has a bismuth content of at least 35% w/w.

24. The method according to claim 20 wherein said polyacrylic acid is present as carbomer.

25. The method according to claim 20 wherein said compound has an infra-red spectra essentially as shown in FIGS. 1 and 2.

* * * * *